US00PP11188P

United States Patent [19]

Kordes

[11] Patent Number: Plant 11,188

[45] Date of Patent: Jan. 25, 2000

[54] MINIATURE ROSE PLANT NAMED 'KORSTIGMA'

[75] Inventor: Wilhelm Kordes, Sparrieshoop, Germany

[73] Assignee: Bear Creek Gardens, Inc., Medford, Oreg.

[21] Appl. No.: 09/046,494

[22] Filed: Mar. 23, 1998

[51] Int. Cl.[7] ..... A01H 5/00

[52] U.S. Cl. ..... Plt./118

[58] Field of Search ..... Plt./118, 125

*Primary Examiner*—Howard J. Locker

*Attorney, Agent, or Firm*—Klarquist Sparkman Campbell Leigh & Whinston, LLP

[57] ABSTRACT

A rose plant of the miniature class, a mutation of the variety 'KORklevia' having a different flower color, smaller flowers with more petals and no glands on the peduncle as compared to its parent.

1 Drawing Sheet

The present invention relates to a new and distinct variety of rose plant of the miniature class which was originated by me by discovering in a greenhouse in Sparrieshoop, Germany in November 1996, a novel flower color mutation of the variety 'KORkleiva'(unpatented).

'KORstigma' distinguishes from its parent in the following characteristics:

1. A different and novel flower color;
2. Slightly smaller flowers;
3. No glands on the peduncle;
4. More petals in its flowers.

Asexual reproduction of this new variety by cutting propagation, as performed at Sparrieshoop, Germany and Somis and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Parent.*—Spontaneous mutant of 'KORkleiva' (unpatented).

Classification:

*Botanical.*—*Rosa hybrida.*

*Commercial.*—Miniature.

Flower

Observations made from specimens grown in a greenhouse environment at Sparrieshoop, Germany and at Somis, Calif. from January, 1997 to December, 1997.

Blooming habit: Continuous.

Bud:

*Size.*—Three-quarter inches long when the petals start to unfurl.

*Form.*—The bud form is long, pointed ovoid.

*Color.*—When sepals first divide, bud color is Yellow Group 12C. When half blown, the upper sides of the petals are Yellow Group 12D on the petal edges changing to Yellow Group 12C in the center of the petal. Outer petals are all Yellow Group 12D. The lower sides of the petals are Yellow Group 12D on the petal edges changing to Yellow Group 12C on the rest of the petal. Outer petals are all Yellow Group 12D.

*Sepals.*—Color: Green group 138B. Surface texture: Covered in fine hairs. There are three lightly appendaged sepals. There are two unappendaged sepals with hairy edges.

*Receptacle.*—Color: Green Group 146C. Shape: Funnel. Size: Small (3/8"×5/16"). Surface: Smooth.

*Peduncle.*—Length: Short (1¼"). Surface: Smooth. Color: Green Group 137C. Strength: Stiff, erect.

Bloom:

*Size.*—Small. Average open size is 1½ inches.

*Borne.*—Singly.

*Stems.*—Short (5"), strong.

*Form.*—When first open: High centered. Permanence: Retains its form to the end; outer petal edges curl back.

*Petalage.*—Number of petals under normal conditions: 35-40.

*Color.*—The upper sides of the outer petals are Yellow-Orange Group 12D, the inner petals are Yellow Group 12D on the edges and Yellow Group 12C toward the middle of each petal. The reverse sides of the outer petals are Yellow Group 12D, the inner petals are Yellow Group 12D on the edges and Yellow Group 12C toward the middle of each petal. The base of each petal has a small (3/16"×3/16"), Yellow Group 12A, half moon at the point of attachment. The major color on the upper sides is Yellow Group 12C to Yellow Group 12D.

*Variegations.*—Occasional greenish-white streaks on the guard petals.

*Discoloration.*—At the end of the first day: No change. At the end of the third day: Fading from Yellow Group 12C to 12D. By day ten, the entire flower is Yellow Group 12D and remains that way to petal drop near day 25.

*Fragrance.*—None.

Petals:

*Texture.*—Thick, leathery.

*Shape.*—Round.

*Form.*—Tips slightly recurved.

*Arrangement.*—Imbricated. Petaloids in the center are few and small.

*Persistence.*—Drop off cleanly before drying.

*Lastingness.*—On the plant: Very long (twenty-five days). As a cut flower: Very long (twenty-five days).

Reproductive Parts:

*Anthers.*—Size: Medium. Quantity: Few. Color: Yellow. Arrangement: Regular around styles, mixed with petaloids.

*Filaments.*—Color: Yellow.

*Pollen.*—Color: Gold yellow.

*Styles.*—Color: Reddish.

*Stigmas.*—Color: Greenish-white.

Plant:

*Form.*—Bush.

*Growth.*—Vigorous; upright; branching; compact.

*Mature Plant.*—At maturity, height is twenty-four inches, width is eighteen inches as a garden rose. When grown as a pot rose in a 4"×3½" pot, the plant is seven inches in height and six inches wide.

Foliage: Number of leaflets on normal mid-stem leaves: Five.

*Size.*—Small. (3"×2").

*Quantity.*—Abundant.

*Color.*—New foliage: Upper and lower surfaces: Greyed-Red Group 178C. Old foliage: Upper surface: Green Group 139A. Lower surface: Green Group 139C.

*Shape.*—Pointed oval.

*Texture.*—Upper side: Glossy, smooth.

*Edge.*—Serrated.

*Serration.*—Single, small.

*Petiole rachis.*—Color: Greyed-Purple Color 183C.

*Petiole underside.*—Smooth, with occasional prickles.

*Stipules.*—Short (5/16"); serrated, bearded.

*Disease resistance.*—Resistant to mildew under normal growing conditions at Sparrieshoop, Germany and Somis, Calif.

Wood:

*New wood.*—Color: Greyed-Purple Color 183A. Bark: Smooth.

*Old wood.*—Color: Green Group 137B. Bark: Smooth.

Prickles:

*Quantity.*—On main canes from base: Few. On laterals from main canes: Few.

*Form.*—Short; straight to hooked slightly downward.

*Color when young:*—Greyed-Purple Color 183B.

Small Prickles:

*Quantity.*—On main stalks: None. On laterals: None.

I claim:

1. A new and distinct variety of rose plant of the miniature class, substantially as herein shown and described as a mutant of the variety 'KORklevia' characterized particularly as to novelty by its difference in flower color, smaller flowers with more petals and no glands on the peduncle as compared to its parent.

* * * * *

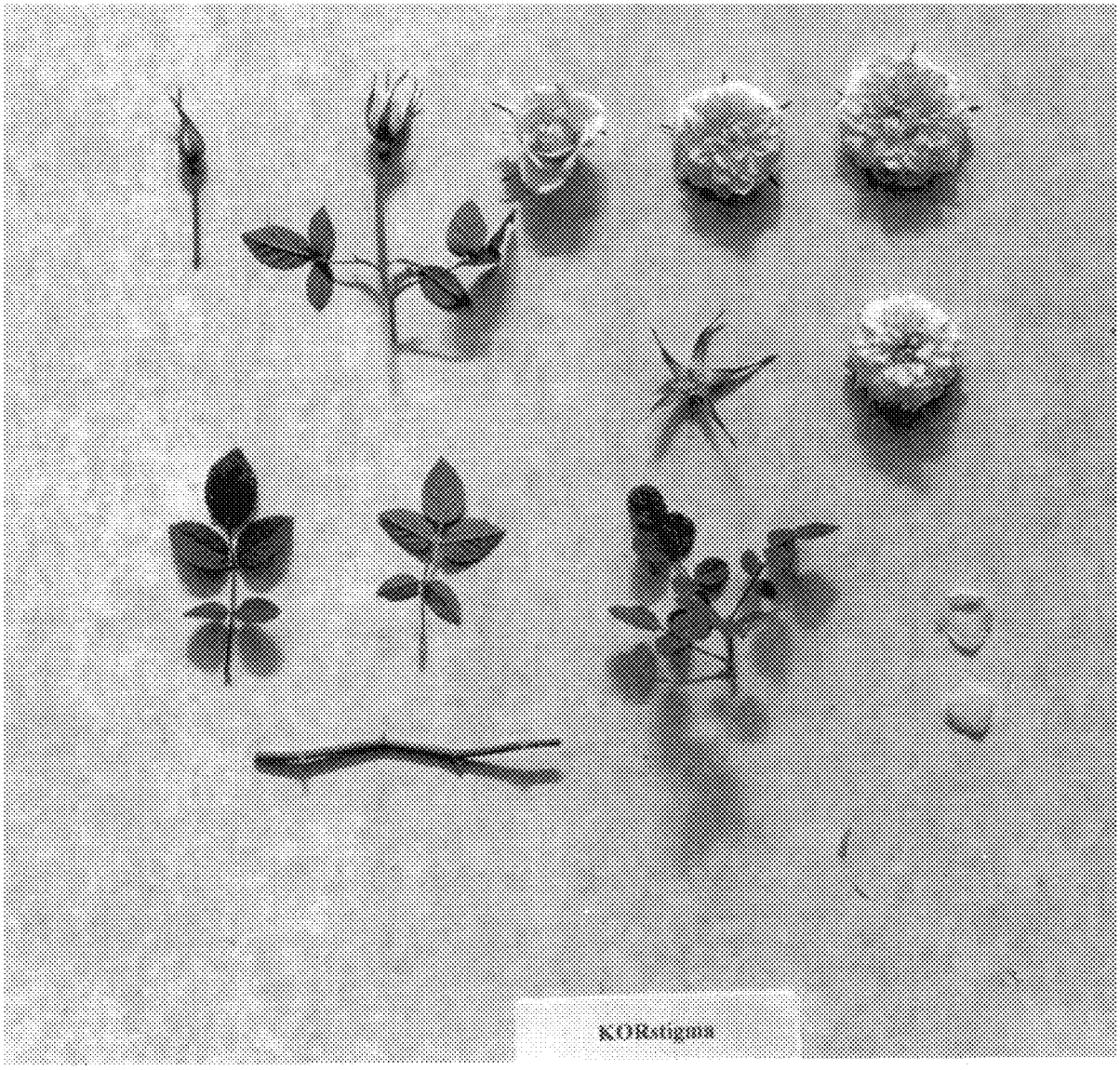
KORstigma

UNITED STATES PATENT AND TRADEMARK OFFICE

CERTIFICATE OF CORRECTION

PATENT NO. : PP11,188
DATED : January 25, 2000
INVENTOR(S) : Wilhelm Kordes

It is certified that error appears in the above-identified patent and that said Letters Patent is hereby corrected as shown below:

In the Abstract:
Line 2 Reads "KORklevia". It should read --KORkleiva--.

In the Specification:
Column 3,
Line 21, reads "Small. (3"x2").". It should read --Small (3"x2").--.

In the Claims:
Column 4,
Line 23, reads "KORklevia". It should read --KORkleiva--.

Signed and Sealed this

Third Day of July, 2001

Nicholas P. Godici

*Attest:*

*Attesting Officer*

NICHOLAS P. GODICI
*Acting Director of the United States Patent and Trademark Office*